US012643872B2

(12) United States Patent　　　　(10) Patent No.:　US 12,643,872 B2
Riedel et al.　　　　　　　　　　　　(45) Date of Patent:　　　Jun. 2, 2026

(54) H₂O₂ WITHOUT DIBC FOR PO PRODUCTION

(71) Applicants:BASF SE, Ludwigshafen am Rhein (DE); Dow Global Technologies LLC, Midland, MI (US)

(72) Inventors: Dominic Riedel, Ludwigshafen am Rhein (DE); Joaquim Henrique Teles, Ludwigshafen am Rhein (DE); Jaroslaw Michael Mormul, Ludwigshafen am Rhein (DE); Andrei-Nicolae Parvulescu, Ludwigshafen am Rhein (DE); Meinolf Weidenbach, Stade (DE); Franciscus Johannes Robertus Van Neer, Hoek (NL)

(73) Assignees: BASF SE, Ludwigshafen am Rhein (DE); Dow Global Technologies LLC, Midland, MI (US)

( * ) Notice:　Subject to any disclaimer, the term of this patent is extended or adjusted under 35 U.S.C. 154(b) by 923 days.

(21) Appl. No.:　17/911,673

(22) PCT Filed:　Mar. 22, 2021

(86) PCT No.:　PCT/EP2021/057238
　　§ 371 (c)(1),
　　(2) Date:　Sep. 15, 2022

(87) PCT Pub. No.: WO2021/191134
　　PCT Pub. Date: Sep. 30, 2021

(65) Prior Publication Data
　　US 2023/0145404 A1　　May 11, 2023

(30) Foreign Application Priority Data
　　Mar. 23, 2020　(EP) ..................................... 20164932

(51) Int. Cl.
　　*C07D 301/12*　　　(2006.01)
(52) U.S. Cl.
　　CPC .................................. *C07D 301/12* (2013.01)
(58) Field of Classification Search
　　CPC .............................. C07D 301/12; Y02P 20/52
　　　　　　　　(Continued)

(56) References Cited

U.S. PATENT DOCUMENTS

| | | |
|---|---|---|
| 5,684,170 A | 11/1997 | Saxton et al. |
| 2003/0078160 A1 | 4/2003 | Hasenzahl et al. |
| 2019/0169149 A1 | 6/2019 | Teles et al. |

FOREIGN PATENT DOCUMENTS

| | | |
|---|---|---|
| EP | 1122249 A1 | 8/2001 |
| EP | 1138387 A1 | 10/2001 |

(Continued)

OTHER PUBLICATIONS

Yueyang Zhongshun Chemical, "Certificate of Analysis", Mar. 18, 2014, 1 page.
International Preliminary Report on Patentability received for PCT Patent Application No. PCT/EP2021/057238, mailed on Jun. 2, 2022, 6 pages.
International Search Report and Written Opinion received for PCT Patent Application No. PCT/EP2021/057238, mailed on Apr. 21, 2021, 8 pages.
Goor et al., "Hydrogen Peroxide," Ullmann's Encyclopedia of Industrial Chemistry, 5th edition, vol. A13, 1989, pp. 443-466.
Stallmach et al., "Spin Echo NMR Diffusion Studies," Annual Reports on NMR Spectroscopy, vol. 61, 2007, pp. 51-131.

(Continued)

*Primary Examiner* — Taylor V Oh
(74) *Attorney, Agent, or Firm* — Faegre Drinker Biddle & Reath LLP

(57)　　　　　　ABSTRACT

The invention relates in a first aspect to a process for the preparation of propylene oxide, comprising: (i) providing a reaction mixture comprising propylene, water, organic solvent, and hydrogen peroxide; (ii) contacting the reaction mixture provided in (i) in an epoxidation zone with an epoxidation catalyst comprising a zeolitic material having a framework structure comprising Si, O, and Ti, and subjecting the reaction mixture to epoxidation reaction conditions in the epoxidation zone, obtaining, in the epoxidation zone, a mixture comprising propylene oxide, water, and organic solvent; (iii) removing an effluent stream from the epoxidation zone, the effluent stream comprising propylene oxide, water, and organic solvent; wherein the reaction mixture provided in (i) and subjected to (ii) contains in an amount of at most 500 mg per kg hydrogen peroxide comprised in said reaction mixture at least one aliphatic oxygen containing compound having 8 to 10 carbon atoms. The invention further relates in a second aspect to a reaction mixture for preparing propylene oxide, comprising propylene, water, organic solvent, and hydrogen peroxide, wherein the reaction mixture comprises at least one aliphatic oxygen containing compound having 8 to 10 carbon atoms in an amount of at most 500 mg per kg hydrogen peroxide comprised in the reaction mixture. In a third aspect, the invention relates to a system comprising an epoxidation catalyst comprising a zeolitic material having a framework structure comprising Si, O, and Ti, and further comprising the reaction mixture comprising propylene, water, and organic solvent according to the second aspect. In a fourth aspect, the invention relates to the use of an aqueous hydrogen peroxide solution as epoxidation agent for preparing propylene oxide in the presence of an organic solvent and an epoxidation catalyst comprising a zeolitic material having a framework structure comprising Si, O, and Ti, wherein the aqueous hydrogen peroxide solution comprises at least one aliphatic oxygen containing compound having 8 to 10 carbon atoms in an amount of at most 500 mg per kg hydrogen peroxide comprised in the aqueous hydrogen peroxide solution.

16 Claims, No Drawings

(58) Field of Classification Search
USPC ......................................................... 549/531
See application file for complete search history.

(56) References Cited

FOREIGN PATENT DOCUMENTS

| EP | 1546035 | A1 | 6/2005 |
| WO | 99/40024 | A1 | 8/1999 |
| WO | 99/48882 | A1 | 9/1999 |
| WO | 99/48883 | A1 | 9/1999 |
| WO | 02/00634 | A1 | 1/2002 |
| WO | 02/00635 | A1 | 1/2002 |
| WO | 02/92586 | A1 | 11/2002 |
| WO | 2004/028962 | A1 | 4/2004 |
| WO | WO 2008122503 | A1 † | 10/2008 |
| WO | 2013/160163 | A1 | 10/2013 |
| WO | 2015/010990 | A1 | 1/2015 |
| WO | 2015/049327 | A1 | 4/2015 |
| WO | 2018/197234 | A1 | 11/2018 |

OTHER PUBLICATIONS

Cox, J. and Ramsay, O., "Mechanisms of Nucleophilic Substitution in Phosphate Esters," Chemical Reviews, vol. 64, No. 4, pp. 317-352, Jul. 24, 1964.†

† cited by third party

H₂O₂ WITHOUT DIBC FOR PO PRODUCTION

CROSS-REFERENCE TO RELATED APPLICATIONS

This application is a national stage application (under 35 U.S.C. § 371) of PCT/EP2021/057238, filed Mar. 22, 2021, which claims benefit of European Application No. 20164932.4, filed Mar. 23, 2020, both of which are incorporated herein by reference in their entirety.

The invention relates in a first aspect to a process for the preparation of propylene oxide comprising: (i) providing a reaction mixture comprising propylene, water, organic solvent, and hydrogen peroxide; (ii) contacting the reaction mixture provided in (i) in an epoxidation zone with an epoxidation catalyst comprising a zeolitic material having a framework structure comprising Si, O, and Ti, and subjecting the reaction mixture to epoxidation reaction conditions in the epoxidation zone, obtaining, in the epoxidation zone, a mixture comprising propylene oxide, water, and organic solvent; (iii) removing an effluent stream from the epoxidation zone, the effluent stream comprising propylene oxide, water, and organic solvent; wherein the reaction mixture provided in (i) and subjected to (ii) contains in an amount of at most 500 mg per kg hydrogen peroxide comprised in said reaction mixture at least one aliphatic oxygen containing compound having 8 to 10 carbon atoms. The invention further relates in a second aspect to a reaction mixture for preparing propylene oxide, comprising propylene, water, organic solvent, and hydrogen peroxide, wherein the reaction mixture comprises at least one aliphatic oxygen containing compound having 8 to 10 carbon atoms in an amount of at most 500 mg per kg hydrogen peroxide comprised in the reaction mixture. In a third aspect, the invention relates to a system comprising an epoxidation catalyst comprising a zeolitic material having a framework structure comprising Si, O, and Ti, and further comprising the reaction mixture comprising propylene, water, and organic solvent according to the second aspect. In a fourth aspect, the invention relates to the use of an aqueous hydrogen peroxide solution as epoxidation agent for preparing propylene oxide in the presence of an organic solvent and an epoxidation catalyst comprising a zeolitic material having a framework structure comprising Si, O, and Ti, wherein the aqueous hydrogen peroxide solution comprises at least one aliphatic oxygen containing compound having 8 to 10 carbon atoms in an amount of at most 500 mg per kg hydrogen peroxide comprised in the aqueous hydrogen peroxide solution.

Propylene oxide is an important intermediate in the chemical industry. A suitable process for the preparation of propylene oxide starts from propylene and makes use of hydrogen peroxide (H₂O₂) as oxidizing agent, of a solvent and of an epoxidation catalyst comprising a titanium zeolite. Hydrogen peroxide is often prepared in the form of aqueous solutions, wherein different processes are known. One widely used process is the so called anthraquinone process ("AO process", see Ullmann's Encyclopedia of Industrial Chemistry, 5th edition, volume A 13 (1989) pages 443-466). The hydrogen peroxide solutions produced by the anthraquinone process are obtained by extracting the so-called oxidized working solution with water. The oxidized working solution is a mixture comprising solvents, anthraquinones, tetrahydroanthraquinones and H₂O₂ obtained by oxidizing the reduced working solution, which is in turn a mixture comprising solvents, anthrahydroquinones, tetrahydroanthrahydroquinone and oxygen (O₂). The thus obtained aqueous solution can be directly used in the epoxidation of propylene. Alternatively, the solution can be concentrated by partial evaporation of the water to obtain H₂O₂ solutions with a higher concentration. Such solutions always contain organic impurities stemming from the working solution. These can be either components of the working solution or products formed by unwanted reactions of these components, like for instance oxidation or hydrolysis products. The exact nature of all organic impurities contained in an aqueous H₂O₂ solution is usually not known and the state of the art contains no or very little information in this respect. Usually the content of organic material is just given in form of a TOC value (total organic carbon), which typically is in the range between 100 and 1000 ppm (mg of organic carbon per kg of H₂O₂ solution). It could however be expected that the nature of the impurities contained in an aqueous H₂O₂ solution will strongly depend on the nature of the solvent system and of the anthraquinone used. The working solution generally consists of a mixture of two solvents to keep both the anthraquinone and the anthrahydroquinone forms, as well as the tetrahydroanthraquinone and tetrahydroanthrahydroquinone forms, in solution, wherein the two solvents are selected from quinone solvents and hydroquinone solvents as, for example, disclosed on page 447 of Ullmann's Encyclopedia of Industrial Chemistry cited above, including, inter alia, ureas as quinone solvent.

Methods are known in the art to remove organic impurities from aqueous H₂O₂ solutions, for instance in the production of electronic grade H₂O₂, but such processes are very expensive and the aqueous H₂O₂ solutions thus obtained are far too expensive to be economically viable to be used in the epoxidation of propylene.

Regarding specific impurities, it is known that aqueous hydrogen peroxide solutions containing amines like dibutylamine (see EP 1 546 035 A1, Evonik) are less well suited to be used in the epoxidation of propylene catalyzed by titanium containing silicates such as titanium silicalite-1 (TS-1) and using methanol as the solvent. Since dibutylamine is generated from tetrabutyl urea, that is commonly used as a solvent component in industrial processes, the state of the art recommends using hydrogen peroxide from a process which does not use a solvent capable of forming amines. Other organic impurities contained in commercial hydrogen peroxide solutions have been mentioned. However, such organic impurities, aside from the amines originating from solvents such as tetra alkyl ureas, have never been reported to have an influence on the epoxidation reaction. Moreover, WO 99/40024 A1 (Solvay SA) as well as WO 2013/160163 A1 (Solvay SA) mention inter alia diisobutylcarbinol as a suitable polar solvent to be used in the manufacture of hydrogen peroxide by the AO-process (see WO 99/40024 A1 page 7, line 14 and WO 2013/160163 A1, page 29, line 30). Thus, it can be concluded that a compound such as diisobutylcarbinol has never been considered as detrimental for the AO process and consequently also not for subsequent reactions such as the epoxidation of propylene. "Diisobutyl carbinol" (DIBC) in technical grade comprises the two isomers 2,6-dimethyl-4-heptanol and 4,6-dimethyl-2-heptanol.

However, due to the importance of propylene oxide for industrial-scale processes, it is desired to carry out the epoxidation reaction using hydrogen peroxide as efficiently as possible.

Therefore, it was an object of the present invention to provide an economically advantageous process for the preparation of propylene oxide from propylene and hydrogen peroxide in an organic solvent which allows to increase the efficiency of the epoxidation reaction.

Surprisingly, it was found that aliphatic oxygen containing compounds having 8 to 10 carbon atoms, which are contained in commercial hydrogen peroxide solutions have a negative impact on the efficiency of the epoxidation of propylene, especially on the catalytic performance of the epoxidation catalyst in the propylene oxide formation process.

Therefore, the invention relates in a first aspect to a process for the preparation of propylene oxide, comprising (i) providing a reaction mixture comprising propylene, water, organic solvent, and hydrogen peroxide;

(ii) contacting the reaction mixture provided in (i) in an epoxidation zone with an epoxidation catalyst comprising a zeolitic material having a framework structure comprising Si, O, and Ti, and subjecting the reaction mixture to epoxidation reaction conditions in the epoxidation zone, obtaining, in the epoxidation zone, a mixture comprising propylene oxide, water, and organic solvent;

(iii) removing an effluent stream from the epoxidation zone, the effluent stream comprising propylene oxide, water, and organic solvent;

wherein the reaction mixture provided in (i) and subjected to (ii) contains in an amount of at most 500 mg per kg hydrogen peroxide comprised in said reaction mixture at least one aliphatic oxygen containing compound having 8 to 10 carbon atoms.

It goes without saying that a sequence of steps (i), (ii) and (iii) means that step (ii) is carried out after, preferably directly after, step (i) and that step (iii) is carried out after, preferably directly after, step (ii). "Directly after" means that no intermediate steps are carried out between (i) and (ii) and between (ii) and (iii).

The expression "the reaction mixture provided in (i) and subjected to (ii) contains in an amount of at most 500 mg per kg hydrogen peroxide comprised in said reaction mixture at least one aliphatic oxygen containing compound having 8 to 10 carbon atoms" means that the reaction mixture only contains one or more aliphatic oxygen containing compounds having 8 to 10 carbon atoms in an amount up to 500 mg per kg hydrogen peroxide comprised in said reaction mixture—the sum of all aliphatic oxygen containing compounds having 8 to 10 carbon atoms contained in the reaction mixture is at most 500 mg per kg hydrogen peroxide comprised in said reaction mixture. In other words, the reaction mixture provided in (i) and subjected to (ii) contains one or more aliphatic oxygen compound having 8 to 10 carbon atoms in an amount which is 500 mg per kg of hydrogen peroxide comprised in reaction mixture (i). The same applies with respect to definitions including specific amount ranges as given hereinbelow.

Preferably, the reaction mixture provided in (i) and subjected to (ii) contains the at least one aliphatic oxygen containing compound having 8 to 10 carbon atoms in an amount in the range from 0 to 500 mg per kg hydrogen peroxide comprised in the reaction mixture, preferably in the range from 0 to 400 mg per kg hydrogen peroxide comprised in the reaction mixture, more preferably in the range from 0 to 300 mg per kg hydrogen peroxide comprised in the reaction mixture, more preferably in the range from 0 to 200 mg per kg hydrogen peroxide comprised in the reaction mixture, more preferably in the range from 0 to 100 mg per kg hydrogen peroxide comprised in the reaction mixture.

It was surprisingly found that the epoxidation catalyst's performance increases with decreasing concentration of the at least one aliphatic oxygen containing compound having 8 to 10 carbon atoms. At concentrations above 500 mg of the at least one aliphatic oxygen containing compound having 8 to 10 carbon atoms per kg hydrogen peroxide, a much higher temperature in the epoxidation zone (and thus a higher temperature of the cooling medium) was required in order to keep the hydrogen peroxide conversion at a value of ≥90%. However, at these high concentrations, selectivity was well below 85%. It was also found that a too high concentration of the at least one aliphatic oxygen containing compound having 8 to 10 carbon atoms of more than 500 mg per kg hydrogen peroxide negatively affected different types of TS-1 zeolite catalysts, independent from their mode of preparation and characteristics. This finding is somewhat surprising since normally different types of TS-1 zeolite catalysts react differently in view of impurities. Experiments further showed that a high hydrogen peroxide conversion of ≥98% and a high selectivity could only be achieved over a meaningful period of time, i.e. for more than 200 hours, if the concentration of the at least one aliphatic oxygen containing compound having 8 to 10 carbon atoms was kept at or below the threshold of 500 ppm.

The at Least One Aliphatic Oxygen Containing Compound Having 8 to 10 Carbon Atoms Generally, there are no specific restrictions regarding the nature of the at least one aliphatic oxygen containing compound having 8 to 10 carbon atoms. The expression "having 8 to 10 carbon atoms" means that each aliphatic oxygen containing compound has 8, 9 or 10 carbon atoms. Preferably, the at least one aliphatic oxygen containing compound having 8 to 10 carbon atoms is selected from the group consisting of secondary mono alcohols $C_nH_{2n+2}O$ with n being an integer in the range of from 8 to 10, mono ketones $C_mH_{2m}O$ with m being an integer in the range of from 8 to 10, diols $C_pH_{2p+2}O_2$ with p being an integer in the range of from 8 to 10, and mixtures of two or more of these compounds; preferably from the group consisting of secondary mono alcohols $C_9H_{20}O$, mono ketones $C_9H_{18}O$, diols $C_9H_{20}O$, and mixtures of two or more of these compounds. The diols $C_9H_{20}O_2$ preferably have one secondary and one tertiary hydroxyl group and are more preferably selected from the group consisting of 2,6-dimethylheptane-2,4-diol, 4,6-dimethylheptane-2,4-diol, 2,4-dimethylheptane-2,6-diol and mixtures of two or more of these diols, each thereof having one secondary and one tertiary hydroxyl group. More preferably, the at least one aliphatic oxygen containing compound having 8 to 10 carbon atoms is selected from the group consisting of secondary mono alcohols $C_9H_{20}O$, mono ketones $C_9H_{18}O$, and mixtures of secondary mono alcohols $C_9H_{20}O$ and mono ketones $C_9H_{18}O$. More preferably, the at least one aliphatic oxygen containing compound having 8 to 10 carbon atoms is selected from the group of diisobutyl carbinol and diisobutyl ketone and mixtures of diisobutyl carbinol and diisobutyl ketone, wherein the at least one aliphatic oxygen containing compound having 8 to 10 carbon atoms more preferably comprises at least diisobutyl carbinol ($C_9H_{19}OH$).

In one embodiment, the at least one aliphatic oxygen containing compound having 8 to 10 carbon atoms comprises diisobutyl carbinol in an amount in the range from 95 to 99.5 weight-%, preferably in the range from 96 to 99 weight-%, based on the total weight of the at least one aliphatic oxygen containing compound having 8 to 10 carbon atoms. In one embodiment, the at least one aliphatic oxygen containing compound having 8 to 10 carbon atoms comprises diisobutyl carbinol in an amount in the range from 95 to 99.5 weight-% and diisobutyl ketone ($C_9H_{18}O$) in an amount in the range from 1.0 to 0.01 weight-%, based on the total weight of the at least one aliphatic oxygen containing compound having 8 to 10 carbon atoms. Preferably, the at least one aliphatic oxygen containing compound having 8 to 10 carbon atoms comprises diisobutyl carbinol in an amount in the range from 96 to 99 weight-% and diisobutyl ketone in an amount in the range from 0.9 to 0.05 weight-%, each based on the total weight of the at least one aliphatic oxygen containing compound having 8 to 10 carbon atoms. The remaining amount up to 100 weight-%, which amounts usually to ≤1 weight-%, comprises compounds such as methylheptane-3-ol, isomers of methylheptane-3-ol and smaller fragments like C4-C6 alcohols and ketones. "Diisobutyl carbinol" (DIBC) comprises the two isomers 2,6-dimethyl-4-heptanol and 4,6-dimethyl-2-heptanol. Preferably ≥95 weight-%, more preferably ≥96 weight-%, more preferably ≥80 weight-%, of the diisobutyl carbinol consist of 2,6-dimethyl-4-heptanol and 4,6-dimethyl-2-heptanol, based on the total weight of the diisobutyl carbinol. In one embodiment, DIBC comprises 80 to 90 weight-%, preferably 82 to 89 weight-%, more preferably 84 to 88 weight-% 4,6-dimethyl-2-heptanol and 10 to 20 weight-%, preferably 11 to 18 weight-%, more preferably 12 to 16 weight-% of 4,6-dimethyl-2-heptanol, based on the total weight of the diisobutyl carbinol. "Diisobutyl ketone" comprises the two isomers 2,6-dimethyl-4-heptanone and 4,6-dimethyl-2-heptanone.

According to step (i) of the process for the preparation of propylene oxide, a reaction mixture comprising propylene, water, organic solvent, and hydrogen peroxide is provided.

Generally, it is conceivable to use a pure or essentially pure propylene as starting material and as part of the reaction mixture provided in (i). Preferably, a mixture of propylene and propane is used. Most preferably a technical propylene grade according to an international norm like for instance ASTM D5273 or DIN 51622 is used. If a mixture of propylene and propane is used as part of the reaction mixture provided in (i), the weight ratio of propylene:propane is preferably at least 7:3. For example, commercially available propylene can be employed which may be either a polymer grade propylene or a chemical grade propylene. Typically, polymer grade propylene has a propylene content in the range of from 99 to 99.8 weight-% and a propane content in the range of from 0.2 to 1 weight-%. Chemical grade propylene typically has a propylene content in the range of from 92 to 98 weight-% and a propane content in the range of from 2 to 8 weight-%. According to a preferred embodiment of the present invention, a mixture of propylene and propane is used which has a propylene content in the range of from 99 to 99.8 weight-% and a propane content in the range of from 0.2 to 1 weight-%.

The organic solvent is preferably an organic epoxidation solvent, more preferred the organic solvent is selected from the group consisting of alcohol, acetonitrile, tert-butanol, propionitrile and mixtures of two or more thereof; more preferred selected from the group consisting of alcohol, acetonitrile and mixtures of alcohol and acetonitrile; more preferred the organic solvent comprises at least an alcohol. The "organic solvent comprises at least an alcohol", means that at least 90 weight-%, preferably at least 95 weight-%, more preferred at least 98 weight-%, more preferred at least 99 weight-% of the organic solvent consists of the alcohol, based on the overall weight of the organic solvent. The alcohol is preferably a C1 to C5 mono alcohol or a mixture of two or more C1 to C5 alcohols, more preferred the alcohol comprises at least methanol, more preferred the alcohol is methanol. According to a preferred embodiment, the organic solvent is methanol.

No restrictions exist regarding the water used for the reaction mixture. It is conceivable to use, for example, water which is treated with $NH_3$ but water not having been treated with $NH_3$ can also be used. Preferably deionized water is used for the reaction mixture. The deionized water can be obtained using ion-exchangers of using condensate. Typical grades of deionized water are defined in ISO 3696 of 1987 and all grades described there can be used within the scope of this invention. The water may additionally contain traces of corrosion inhibiting additives like ammonia, hydrazine or hydroxylamine in which case it should have a pH value in the range of 7 to 9 (measured with a calibrated glass electrode). Preferably, the water used does not contain corrosion inhibiting additives.

Generally, the reaction mixture comprising propylene, water, organic solvent, and hydrogen peroxide can be provided in (i) according to any conceivable method. Preferably, the reaction mixture comprising propylene, water, organic solvent, and hydrogen peroxide or a source of hydrogen peroxide, provided in (i) is prepared from two or more streams. More preferably, the reaction mixture is provided in (i) by combining at least three individual streams wherein a first stream comprises hydrogen peroxide or a source of hydrogen peroxide, optionally as aqueous solution, a second stream comprises propylene and optionally propane and a third stream comprises the organic solvent and optionally water.

Preferably, the weight ratio of propylene:hydrogen peroxide (w/w) in the reaction mixture provided in (i) is in the range from 1:1 to 6:1, more preferably in the range from 1:1 to 2:1 or in the range from 3:1 to 5:1. Preferably, the weight ratio of organic solvent:hydrogen peroxide (w/w) in the reaction mixture provided in (i) is in the range from 15:1 to 5:1, more preferably in the range from 12:1 to 6:1, more preferably in the range from 11:1 to 8:1. Preferably, the weight ratio of organic solvent:propylene (w/w) in the reaction mixture provided in (i) is in the range from 10:1 to 1:0.1, more preferably in the range from 9:1 to 1:1, more preferably in the range from 9:1 to 7:1 or in the range from 1.5:1 to 1:1.

Preferably, providing the reaction mixture in (i) comprises
    (i.1) providing an aqueous hydrogen peroxide solution;
    (i.2) admixing the aqueous hydrogen peroxide solution provided in (i.1) with propylene and organic solvent, obtaining the reaction mixture;
wherein the aqueous hydrogen peroxide solution provided in (i.1) and subjected to (i.2) contains the at least one aliphatic oxygen containing compound having 8 to 10 carbon atoms in an amount of at most 500 mg per kg hydrogen peroxide comprised in the reaction mixture.

It goes without saying that a sequence of steps (i.1), (i.2) means that step (i.2) is carried out after, preferably directly after, step (i.1). "Directly after" means that no intermediate steps are carried out between (i.1) and (i.2). It is understood that this also means that the complete sequence of steps is preferably (i.1), (i.2), (ii) and (iii) in that order, wherein preferably no intermediate step is carried out between (i.2) and (ii) as well as between (ii) and (iii).

Aqueous Hydrogen Peroxide Solution

Preferably, the aqueous hydrogen peroxide solution provided in (i.1) and subjected to (i.2) contains the at least one aliphatic oxygen containing compound having 8 to 10 carbon atoms in an amount in the range from 0 to 500 mg per kg hydrogen peroxide comprised in the aqueous hydrogen peroxide solution, preferably in the range from 0 to 400 mg per kg hydrogen peroxide comprised in the aqueous hydrogen peroxide solution, more preferably in the range from 0 to 300 mg per kg hydrogen peroxide comprised in the aqueous hydrogen peroxide solution, more preferably in the range from 0 to 200 mg per kg hydrogen peroxide comprised in the aqueous hydrogen peroxide solution, more preferably in the range from 0 to 100 mg per kg hydrogen peroxide comprised in the aqueous hydrogen peroxide solution. The expression "the reaction mixture provided in (i) and subjected to (ii) contains in an amount of at most 500 mg per kg hydrogen peroxide comprised in said reaction mixture at least one aliphatic oxygen containing compound having 8 to 10 carbon atoms" means that the reaction mixture only contains one or more aliphatic oxygen containing compounds having 8 to 10 carbon atoms in an amount up to 500 mg per kg hydrogen peroxide comprised in said reaction mixture—the sum of all aliphatic oxygen containing compounds having 8 to 10 carbon atoms contained in the reaction mixture is at most 500 mg per kg hydrogen peroxide comprised in said reaction mixture. The same applies with respect to definitions including specific amount ranges as given hereinabove.

Preferably, the aqueous hydrogen peroxide solution provided in (i.1) and subjected to (i.2) has a total organic carbon content (TOC) in the range from 100 to 800 mg per kg hydrogen peroxide comprised in the aqueous hydrogen peroxide solution, preferably in the range from 120 to 750 mg per kg hydrogen peroxide comprised in the aqueous hydrogen peroxide solution, more preferably in the range from 150 to 700 mg per kg hydrogen peroxide comprised in the aqueous hydrogen peroxide solution, determined as described in Reference Example 5.

Generally, no specific restrictions exist with respect to the pH value of the aqueous hydrogen peroxide solution and with respect to the amount of hydrogen peroxide contained in the solution provided that the epoxidation of propylene can be carried out efficiently. Preferably, the aqueous hydrogen peroxide solution provided in (i.1) and subjected to (i.2) has a pH in the range from 0 to 3.0, preferably in the range from 0.1 to 2.5, more preferably in the range from 0.5 to 2.3, determined as described in Reference Example 4. Preferably, the aqueous hydrogen peroxide solution provided in (i.1) and subjected to (i.2) comprises from 20 to 80 weight-%, preferably from 30 to 70 weight-%, more preferably from 40 to 60 weight-% of hydrogen peroxide relative to the total weight of the aqueous hydrogen peroxide solution.

Generally, no specific restrictions exist with respect to the origin of the aqueous hydrogen peroxide solution provided that the epoxidation of propylene can be carried out efficiently. Preferably, the aqueous hydrogen peroxide solution provided in (i.1) and subjected to (i.2) is obtained or obtainable from an anthraquinone process.

According to one embodiment of the present invention, it is preferred to employ an aqueous hydrogen peroxide solution, which is obtained as crude hydrogen peroxide solution by extraction of a mixture which results from a process known as anthraquinone process (see, e.g., Ullmann's Encyclopedia of Industrial Chemistry, 5$^{th}$ edition, volume A 13 (1989) pages 443-466), wherein a solution of an anthraquinone is used containing an alkyl group preferably having of from 2 to 10 carbon atoms, more preferably a 2-6 carbon atoms, more preferably 2, 5 or 6 carbon atoms, and where the solvent used usually consists of a mixture of at least two different solvents. Preferably, mixtures of two solvents or mixtures of three solvents are used. Preferably none of the solvents used in the anthraquinone process is a nitrogen containing substance. This solution of the anthraquinone is usually referred to as the working solution. In this process, the hydrogen peroxide formed in the course of the anthraquinone process is generally separated by extraction from the respective working solution after a hydrogenation/reoxidation cycle. Said extraction can be performed preferably with essentially pure water, and the crude aqueous hydrogen peroxide solution is obtained. It is generally possible to further purify and/or concentrate the thus obtained crude aqueous hydrogen peroxide solution by distillation. It is possible to use crude aqueous hydrogen peroxide solution which has not been subjected to purification and/or concentration by distillation and it is also possible to use an aqueous hydrogen peroxide solution which has been subjected to purification and/or concentration by distillation. Further, it is generally possible to subject the crude aqueous hydrogen peroxide solution to a further extraction stage wherein a suitable extracting agent, preferably an organic solvent is used. More preferably, the organic solvent used for this further extraction stage is the same solvent which is used in the anthraquinone process. Preferably the extraction is performed using just one of the solvents in the working solution and most preferably using just the most nonpolar solvent of the working solution. In case the crude aqueous hydrogen peroxide solution is subjected to such further extraction stage, a so-called crude washed hydrogen peroxide solution is obtained. According to a preferred embodiment of the present invention, the crude washed hydrogen peroxide solution is used as the aqueous hydrogen peroxide solution in (i.1). The production of a crude solution is described, for example, in European patent application EP 1 122 249 A1. As to the term "essentially pure water", reference is made to paragraph 10, page 3 of EP 1 122 249 A1 which is incorporated by reference. The hydrogen peroxide can also be treated to remove trace metals, for example, as described in the WO 2015/049327 A1 before use.

It is conceivable that the hydrogen peroxide is prepared in situ in the epoxidation zone from hydrogen and oxygen, preferably in the presence of a suitable noble metal catalyst comprised in the epoxidation zone according to (ii). A suitable noble metal catalyst preferably comprises one or more of palladium, platinum, silver, gold, rhodium, iridium, ruthenium and osmium. Preferably, the noble metal catalyst comprises palladium. The noble metal catalyst is preferably supported on a carrier, wherein the carrier preferably comprises one or more of $SiO_2$, $Al_2O_3$, $B_2O_3$, $GeO_2$, $Ga_2O_3$, $ZrO_2$, $TiO_2$, MgO, carbon and one or more zeolites, preferably one or more titanium zeolites. More preferably, the carrier comprises the epoxidation catalyst comprising a titanium zeolite. If hydrogen peroxide is prepared in the epoxidation zone according to (ii) in situ from hydrogen and oxygen, the reaction mixture provided in (i) comprises propylene, hydrogen, oxygen, water, and organic solvent.

Reaction Conditions in (ii)—Epoxidation

According to step (ii) of the process for the preparation of propylene oxide, the reaction mixture provided in (i) is contacted in an epoxidation zone with an epoxidation catalyst comprising a zeolitic material having a framework structure comprising Si, O, and Ti, and the reaction mixture is subjected to epoxidation reaction conditions in the epoxidation zone, obtaining, in the epoxidation zone, a mixture comprising propylene oxide, water, and organic solvent.

Generally, no specific restrictions exist regarding the conditions under which the contacting in the epoxidation zone with the epoxidation catalyst takes place provided that an efficient epoxidation of propylene takes place. Preferably, the epoxidation reaction conditions according to (ii) comprise trickle-bed conditions or fixed-bed conditions, wherein fixed-bed conditions are more preferred. Preferably, these conditions are applied in a reactor wherein the catalyst is present in a fixed-bed. "Trickle-bed conditions" preferably mean that the reaction is preferably carried out at temperatures and pressures at which the reaction mixture is present partly in a liquid phase and partly in a gaseous phase, with the catalyst being present in a fixed bed. In embodiments with fixed-bed conditions, the reaction is preferably carried out at temperatures and pressures at which the reaction mixture is liquid and no gas phase is present in the epoxidation zone, wherein two or more liquid phases may exist, with the catalyst being present in a fixed bed. Preferably, the contacting of the reaction mixture provided in (i) in the epoxidation zone with the epoxidation catalyst according to (ii) is carried out at an absolute pressure in the epoxidation zone in the range from 0.5 to 5.0 MPa, preferably in the range from 1.5 to 3.0 MPa, more preferably in the range from 1.8 to 2.8 MPa.

Generally, the contacting of the reaction mixture provided in (i) in the epoxidation zone with the epoxidation catalyst according to (ii) can be carried out in any appropriate way. Thus, for example, it can be carried out in a batch reactor or in at least one semi-continuously operated reactor or in at least one continuously operated reactor. The continuous mode of operation is preferred, wherein preferably at least (ii) is carried out continuously, wherein more preferably at least (ii) and (iii), more preferably (i), (ii) and (iii) are carried out continuously.

Preferably, the contacting of the reaction mixture provided in (i) in an epoxidation zone according to (ii) with an epoxidation catalyst is carried out in at least one, preferably continuously operated, reactor such as a tube reactor or a tube bundle reactor which preferably contains at least one cooling jacket surrounding the at least one tube. A cooling medium flows through the cooling jacket. The nature of the cooling medium is not particular restricted as long as it is sufficient for adjusting the temperature in the epoxidation zone. For example, the cooling medium comprises water, wherein it may additionally comprise additives such as aliphatic C2 to C5 mono-alcohols, aliphatic C2 to C5 di-alcohols and mixtures of two or more thereof. Preferably, ≥90 weight-%, more preferred 95 weight-% of the cooling medium are water, based on the total weight of the cooling medium. The temperature of the cooling medium is the temperature of the cooling medium used for adjusting the temperature of the reaction mixture in epoxidation zone according to (ii) wherein it is preferred that said temperature is adjusted by passing the cooling medium through a cooling jacket, wherein the temperature of the cooling medium is preferably the temperature of the cooling medium prior to adjusting the temperature of the reaction mixture, preferably the temperature of the cooling medium at the entrance of the cooling jacket.

Preferably, the contacting of the reaction mixture provided in (i) in the epoxidation zone with the epoxidation catalyst according to (ii) is carried out at a temperature in the epoxidation zone in the range from 33 to 73° C., preferably in the range from 38 to 63° C., more preferably in the range from 53 to 63° C. The temperature in the epoxidation zone is measured with a tenfold thermocouple, i.e. ten thermoelements. The epoxidation zone is defined as the zone where a reaction of hydrogen peroxide and propylene resulting in propylene oxide formation still takes place in a detectable amount (≥10 ppm propylene oxide). Preferably, the epoxidation zone is present over the complete length of the catalyst bed, i.e. is the zone, preferably within a reactor, where the epoxidation catalyst is present (epoxidation zone=catalyst bed). The hotspot, i.e. the zone where maximum reaction takes place, is typically located in the first half of the catalyst bed and preferably six of the ten thermoelements are located in the first half of the catalyst bed.

The temperature in epoxidation zone is the average temperature determined from the temperature values measured by all thermoelements located in the first half of the catalyst bed. Typically, the temperature values measured by these thermoelements differ from each other in the range of from 6 to 10° C.

Preferably, the temperature of the cooling medium is the temperature of the cooling medium at entrance into the reactor. Preferably, the temperature of the cooling medium is in the range from 25 to 65° C., more preferably in the range from 30 to 55° C., more preferably in the range from 345 to 55° C. A temperature of the cooling medium in the range from 45 to 55° C. is the optimum temperature range. Temperatures below 45° C. are related to the start-up stage of the epoxidation reaction and are to low for an efficient tempering during the epoxidation reaction. Above 55° C. the decomposition of hydrogen peroxide and the formation of oxygen increase exponentially. In the range from 45 to 55° C. of the cooling medium, the temperature in the epoxidation zone is in the optimum range of 53 to 63° C. so that a maximum in selectivity and an optimum in activity are reached.

Epoxidation Zone

According to step (ii) of the process for the preparation of propylene oxide, the reaction mixture provided in (i) is contacted in an epoxidation zone with an epoxidation catalyst comprising a zeolitic material having a framework structure comprising Si, O, and Ti, and the reaction mixture is subjected to epoxidation reaction conditions in the epoxidation zone, obtaining, in the epoxidation zone, a mixture comprising propylene oxide, water, and organic solvent.

Generally, there are no specific restrictions regarding the design of the epoxidation zone provided that it is suitable for carrying out a, preferably continuous, epoxidation reaction. Preferably, the epoxidation zone according to (ii) comprises one or more epoxidation subzone wherein a given epoxidation subzone preferably consist of one or more epoxidation reactors wherein, with regard to the design of the one or more epoxidation reactors, no specific restrictions exist provided that the reactors are suitable for carrying out a, preferably continuous, epoxidation reaction.

Preferably, the epoxidation zone according to (ii) comprises a first epoxidation subzone consisting of one or more epoxidation reactors A. The term "first epoxidation subzone" as used in this context of the present invention relates to the epoxidation subzone into which the reaction mixture provided in (i) is passed, wherein the epoxidation zone of (ii) may comprise further epoxidation subzones which are arranged downstream of the first epoxidation subzone. If the first epoxidation subzone consisting of two or more epoxidation reactors A, it is preferred that the two or more epoxidation reactors A are arranged in parallel. In this case, it is preferred that in (ii), the reaction mixture provided in (i) is passed into at least one of the epoxidation reactors A. It is possible, for example, that, while the reaction mixture provided in (i) is passed into at least one of the epoxidation reactors A, at least one of the reactors A is taken out of operation, for example for maintenance purposes and/or for regenerating the catalyst comprised in the at least one of the reactors A. If the first epoxidation subzone comprises two or more epoxidation reactors A, the reactors in operation are operated essentially identically so that in every epoxidation reactor A in operation, a given epoxidation condition is in the same range in every reactor. For example, the temperature in the epoxidation zone is in the same range in every reactor.

The temperature of the cooling medium is the temperature of the cooling medium used for adjusting the temperature of the reaction mixture in the first epoxidation reaction subzone according to (ii) wherein it is preferred that said temperature is adjusted by passing the cooling medium through a cooling jacket of the one or more epoxidation reactors A, wherein the temperature of the cooling medium is preferably the temperature of the cooling medium prior to adjusting the temperature of the reaction mixture, preferably the temperature of the cooling medium at the entrance of the cooling jacket of the one or more epoxidation reactors A. If the first epoxidation subzone comprises two or more epoxidation reactors A, the temperature of the cooling medium relates a given reactor A in operation of the first epoxidation subzone.

According to a first preferred embodiment of the present invention, the epoxidation zone according to (ii) consists of the first epoxidation subzone.

According to a second preferred embodiment of the present invention, the epoxidation zone according to (ii) additionally comprises a second epoxidation subzone consisting of one or more epoxidation reactors B wherein, if the second epoxidation subzone comprises two or more epoxidation reactors B, the two or more epoxidation reactors B are arranged in parallel, wherein the second epoxidation subzone is arranged downstream of the first epoxidation subzone. In this case, it is preferred that the effluent stream obtained from the first epoxidation subzone, optionally after a suitable intermediate treatment, is passed into at least one of the epoxidation reactors B. It is possible, for example, that, while the effluent stream obtained from the first epoxidation subzone, optionally after a suitable intermediate treatment, is passed into at least one of the epoxidation reactors B, at least one of the reactors B is taken out of operation, for example for maintenance purposes and/or for regenerating the catalyst comprised in the at least one of the reactors B. If the second epoxidation subzone comprises two or more epoxidation reactors B, the reactors in operation are operated essentially identically so that in every epoxidation reactor B in operation, a given epoxidation condition is in the same range in every reactor. Generally, it is conceivable that in addition to the first epoxidation subzone and the second epoxidation subzone, the epoxidation zone according to (ii) comprises at least one further epoxidation subzone arranged downstream of the second epoxidation subzone. Preferably, according to the second preferred embodiment of the present invention, the epoxidation zone according to (ii) consists of the first epoxidation subzone and the second epoxidation subzone.

Preferably, the temperature of the reaction mixture in the second epoxidation reaction subzone is not adjusted by passing a cooling medium through a cooling jacket of the one or more epoxidation reactors B. More preferably, the second epoxidation subzone is an essentially adiabatic epoxidation subzone. More preferably, the second epoxidation subzone is an adiabatic epoxidation subzone.

Epoxidation Catalyst

According to step (ii) of the process for the preparation of propylene oxide, the reaction mixture provided in (i) is contacted in an epoxidation zone with an epoxidation catalyst comprising a zeolitic material having a framework structure comprising Si, O, and Ti. Generally, no specific restrictions exists with respect to the epoxidation catalyst comprising a zeolitic material having a framework structure comprising Si, O, and Ti. Preferably, from 95 to 100 weight-%, more preferably from 98 to 100 weight-%, more preferably from 99 to 100 weight-%, more preferably from 99.5 to 100 weight-%, more preferably from 99.9 to 100 weight-% of the zeolitic material consist of Si, O, Ti and optionally H. Preferably, the zeolitic material comprises Ti in an amount in the range from 0.2 to 5 weight-%, more preferably in the range from 0.5 to 4 weight-%, more preferably in the range from 1.0 to 3 weight-%, more preferably in the range from 1.2 to 2.5 weight-%, more preferably in the range from 1.4 to 2.2 weight-%, calculated as elemental Ti and based on the total weight of the zeolitic material.

Preferably, the zeolitic material having a framework structure comprising Si, O, and Ti comprised in the epoxidation catalyst is a titanium zeolite having ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITQ,ITW, IWR, IWW, JBW, KFI, LAU, LEV, LIO, LOS, LOV, LTA, LTL, LTN, MAR, MAZ, MCM-22(S), MCM-36, MCM-56, MEl, MEL, MEP, MER, MIT-1, MMFI, MFS, MON, MOR, MSE, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG, ZON SVR, SVY framework structure or a mixed structure of two or more of these framework types Framework types such as MCM-22(S), MCM-56, IEZ-MWW, ITQ (delaminated MWW), MIT-1, and MCM-36 are titanium zeolites having framework structures related to MWW framework structure, obtained or obtainable therefrom or from the respective two dimensional precursor by, for example, layer expansion and/or postmodification. Preferably the zeolitic material having a framework structure comprising Si, O, and Ti comprised in the epoxidation catalyst is a titanium zeolite having an MFI framework type, an MEL framework type, an MWW framework type, an MCM-22(S) framework type, an MCM-56 framework type, an IEZ-MWW framework type, an MCM-36 framework type, an ITQ framework type, a BEA framework type, a MOR framework type, or a mixed structure of two or more of these framework types, more preferably an MFI framework type, or an MWW framework type, more preferred the zeolitic material having a framework structure comprising Si, O, and Ti has framework type MEl. More preferably, the zeolitic material having a framework structure comprising Si, O, and Ti is a titanium silicalite-1 (TS-1).

The epoxidation catalyst comprising a zeolitic material having a framework structure comprising Si, O, and Ti can be employed in every conceivable form, including a powder, a micropowder, preferably a spray-powder, as a molding comprising a powder, or as a molding comprising a micropowder, preferably a spray-powder. Preferably, the epoxidation catalyst comprising a zeolitic material having a framework structure comprising Si, O, and Ti is employed as a molding comprising a powder or a micropowder, preferably a spray-powder, more preferably as a molding comprising a micropowder, preferably a spray-powder. More preferably, the epoxidation catalyst comprising a zeolitic material having a framework structure comprising Si, O, and Ti is present in the epoxidation zone as a molding, preferably as fluidized-bed catalyst or a fixed-bed catalyst, more preferably as a fixed-bed catalyst.

According to a preferred embodiment, the epoxidation catalyst further comprises a binder. Preferably, the epoxidation catalyst is in the form of a molding, preferably in the form of an extrudate or a granule, wherein the molding preferably comprises the zeolitic material and a binder. Preferably, from 95 to 100 weight-%, preferably from 98 to 100 weight-%, more preferably from 99 to 100 weight-%, more preferably from 99.5 to 100 weight-%, more preferably from 99.9 to 100 weight-% of the molding consist of the zeolitic material and the binder. Preferably, from 95 to 100 weight-%, preferably from 98 to 100 weight-%, more preferably from 99 to 100 weight-%, more preferably from 99.5 to 100 weight-%, more preferably from 99.9 to 100 weight-% of the binder comprised in the molding consist of Si and O.

Preferably, the epoxidation catalyst, preferably the molding, comprises the binder, calculated as $SiO_2$, in an amount in the range from 2 to 90 weight-%, more preferably in the range from 5 to 70 weight-%, more preferably in the range from 10 to 50 weight-%, more preferably in the range from 15 to 30 weight-%, more preferably in the range from 20 to 25 weight-%, based on the total weight of the epoxidation catalyst, preferably based on the total weight of the molding and/or wherein the epoxidation catalyst, preferably the molding, comprises the zeolitic material in an amount in the range of from 10 to 98 weight-%, preferably in the range of from 30 to 95 weight-%, more preferred in the in the range of from 50 to 90 weight-%, more preferred in the range of from 70 to 85 weight-%, more preferred in the range of from 75 to 80 weight-%, based on the total weight of the epoxidation catalyst, preferably based on the total weight of the molding.

Further Process Steps

Subsequent to steps (i), (ii) and (iii) the process for the preparation of propylene oxide may comprise (iv) separating propylene oxide from the effluent stream obtained in (iii), optionally after having separated propylene, obtaining a stream S1 comprising propylene oxide and a stream S2 comprising water and organic solvent.

Preferably, (iv) comprises (iv-1) separating propylene from the effluent stream obtained in (iii) and preferably recycling at least a portion of the separated propylene, optionally after work-up, to the epoxidation zone according to (ii), obtaining a stream S1a comprising propylene oxide, water, and organic solvent and being depleted of propylene compared to the effluent stream;

(iv-2) separating propylene oxide from the stream S1a obtained according to (iv-1), obtaining a stream S1 b comprising propylene oxide and being depleted of water and the organic solvent compared to the effluent stream and stream S1a respectively, and a stream S2 comprising water and organic solvent and being depleted of propylene oxide compared to the effluent stream and S1a respectively.

Subsequent to steps (i), (ii), (iii) and (iv) the process for the preparation of propylene oxide may comprise (v) separating organic solvent from stream S2 obtained according to (iv) or (iv-2) by distillation, obtaining a stream S3 enriched in organic solvent compared to stream S2 and preferably recycling at least a portion of S3, optionally after work-up, to the epoxidation zone according to (ii).

It goes without saying that a subsequent to (i), (ii) and (iii) means that step (iv) is carried out after, preferably directly after, step (iii). "Directly after" means that no intermediate steps are carried out between (iii) and (iv). It is understood that this also means that the complete sequence of steps is preferably (i), (ii), (iii) and (iv) in that order, wherein preferably no intermediate step is carried out between (i) and (ii) as well as between (ii) and (iii) and between (iii) and (iv). The same applies for step (v).

2nd Aspect—Reaction Mixture

In a second aspect, the invention relates to a reaction mixture for preparing propylene oxide, wherein the reaction mixture comprises propylene, water, organic solvent, and hydrogen peroxide, wherein the reaction mixture comprises at least one aliphatic oxygen containing compound having 8 to 10 carbon atoms in an amount of at most 500 mg per kg hydrogen peroxide comprised in the reaction mixture. The expression "the reaction mixture provided in (i) and subjected to (ii) contains in an amount of at most 500 mg per kg hydrogen peroxide comprised in said reaction mixture at least one aliphatic oxygen containing compound having 8 to 10 carbon atoms" means that the reaction mixture only contains one or more aliphatic oxygen containing compounds having 8 to 10 carbon atoms in an amount up to 500 mg per kg hydrogen peroxide comprised in said reaction mixture—the sum of all aliphatic oxygen containing compounds having 8 to 10 carbon atoms contained in the reaction mixture is at most 500 mg per kg hydrogen peroxide comprised in said reaction mixture. The same applies with respect to definitions including specific amount ranges as given hereinbelow. In that second aspect, the at least one aliphatic oxygen containing compound having 8 to 10 carbon atoms is preferably comprised in the reaction mixture in an amount in the range from 0 to 500 mg per kg hydrogen peroxide comprised in the reaction mixture, more preferably in the range from 0 to 440 mg per kg hydrogen peroxide comprised in the reaction mixture, more preferably in the range from 0 to 300 mg per kg hydrogen peroxide comprised in the reaction mixture, more preferably in the range from 0 to 200 mg per kg hydrogen peroxide comprised in the reaction mixture, more preferably in the range from 0 to 100 mg per kg hydrogen peroxide comprised in the reaction mixture. Further details as disclosed above in view of the first aspect of the invention, i.e. the process for preparing propylene oxide, apply also for the reaction mixture for preparing propylene oxide according to the second aspect. The reaction mixture is preferably being obtainable or obtained by a process comprising, preferably consisting of (i) as defined above in view of the first aspect. The invention thus also relates to a process for preparing a reaction mixture according to the second aspect, wherein the reaction mixture comprises, preferably consists of (i) as defined above in view of the first aspect.

3rd Aspect—Catalytic Epoxidation System

In a third aspect, the invention relates to a system, preferably a catalytic epoxidation system, comprising an epoxidation catalyst comprising a zeolitic material having a framework structure comprising Si, O, and Ti, and further comprising the reaction mixture comprising propylene, water, and organic solvent according to the second aspect as described above. The catalytic epoxidation system is preferably obtainable or obtained by a process comprising providing a reaction mixture according to the second aspect and bringing said reaction mixture in contact with the zeolitic material having a framework structure comprising Si, O, and Ti. The reaction mixture comprises, preferably consists of (i) as defined above in view of the first aspect. The invention thus also relates to a process for preparing the catalytic epoxidation system, comprising providing a reaction mixture according to the second aspect and bringing said reaction mixture in contact with the zeolitic material having a framework structure comprising Si, O, and Ti.

4th Aspect—Use

In a fourth aspect, the invention relates to the use of an aqueous hydrogen peroxide solution as epoxidation agent for preparing propylene oxide in the presence of an organic solvent and an epoxidation catalyst comprising a zeolitic material having a framework structure comprising Si, O, and Ti, wherein the aqueous hydrogen peroxide solution comprises at least one aliphatic oxygen containing compound having 8 to 10 carbon atoms in an amount of at most 500 mg per kg hydrogen peroxide comprised in the aqueous hydrogen peroxide solution.

The present invention is further illustrated by the following set of embodiments and combina-tions of embodiments resulting from the dependencies and back-references as indicated. In particular, it is noted that in each instance where a range of embodiments is mentioned, for example in the context of a term such as "The . . . of any one of embodiments 1 to 4", every embodiment in this range is meant to be explicitly disclosed for the skilled person, i.e. the wording of this term is to be understood by the skilled person as being synonymous to "The . . . of any one of embodiments 1, 2, 3, and 4". Further, it is explicitly noted that the following set of embodiments is not the set of claims determining the extent of protection, but represents a suitably structured part of the description directed to general and preferred aspects of the present invention.

1. A process for the preparation of propylene oxide, comprising
   (i) providing a reaction mixture comprising propylene, water, organic solvent, and hydrogen peroxide;
   (ii) contacting the reaction mixture provided in (i) in an epoxidation zone with an epoxidation catalyst comprising a zeolitic material having a framework structure comprising Si, O, and Ti, and subjecting the reaction mixture to epoxidation reaction conditions in the epoxidation zone, obtaining, in the epoxidation zone, a mixture comprising propylene oxide, water, and organic solvent;

(iii) removing an effluent stream from the epoxidation zone, the effluent stream comprising propylene oxide, water, and organic solvent;
   wherein the reaction mixture provided in (i) and subjected to (ii) contains in an amount of at most 500 mg per kg hydrogen peroxide comprised in said reaction mixture at least one aliphatic oxygen containing compound having 8 to 10 carbon atoms.

2. The process of embodiment 1, wherein the reaction mixture provided in (i) and subjected to
   (ii) contains the at least one aliphatic oxygen containing compound having 8 to 10 carbon atoms in an amount in the range from 0 to 500 mg per kg hydrogen peroxide comprised in the reaction mixture, preferably in the range from 0 to 400 mg per kg hydrogen peroxide comprised in the reaction mixture, more preferably in the range from 0 to 300 mg per kg hydrogen peroxide comprised in the reaction mixture, more preferably in the range from 0 to 200 mg per kg hydrogen peroxide comprised in the reaction mixture, more preferably in the range from 0 to 100 mg per kg hydrogen peroxide comprised in the reaction mixture.

3. The process of embodiment 1 or 2, wherein the at least one aliphatic oxygen containing compound having 8 to 10 carbon atoms is selected from the group consisting of secondary mono alcohols $C_nH_{2n+2}O$ with n being an integer in the range of from 8 to 10, mono ketones $C_mH_{2m}O$ with m being an integer in the range of from 8 to 10, diols $C_pH_{2p+2}O_2$ with p being an integer in the range of from 8 to 10, and mixtures of two or more of these compounds; preferably from the group consisting of secondary mono alcohols $C_9H_{20}O$, mono ketones $C_9H_{18}O$, diols $C_9H_{20}O_2$, and mixtures of two or more of these compounds; more preferably selected from the group consisting of secondary mono alcohols $C_9H_{20}O$, mono ketones $C_9H_{18}O$, and mixtures of secondary mono alcohols $C_9H_{20}O$ and mono ketones $C_9H_{18}O$; more preferably selected from the group of diisobutyl carbinol and diisobutyl ketone and mixtures of diisobutyl carbinol and diisobutyl ketone; wherein the at least one aliphatic oxygen containing compound having 8 to 10 carbon atoms more preferably comprises at least diisobutyl carbinol.

4. The process of any one of embodiments 1 to 3, wherein providing the reaction mixture in
   (i) comprises
   (i.1) providing an aqueous hydrogen peroxide solution;
   (i.2) admixing the aqueous hydrogen peroxide solution provided in (i.1) with propylene
   and organic solvent, obtaining the reaction mixture;
   wherein the aqueous hydrogen peroxide solution provided in (i.1) and subjected to (i.2) contains the at least one aliphatic oxygen containing compound having 8 to 10 carbon atoms in an amount of at most 500 mg per kg hydrogen peroxide comprised in the reaction mixture.

5. The process of embodiment 4, wherein the aqueous hydrogen peroxide solution provided in (i.1) and subjected to (i.2) contains the at least one aliphatic oxygen containing compound having 8 to 10 carbon atoms in an amount in the range from 0 to 500 mg per kg hydrogen peroxide comprised in the aqueous hydrogen peroxide solution, preferably in the range from 0 to 400 mg per kg hydrogen peroxide comprised in the aqueous hydrogen peroxide solution, more preferably in the range from 0 to 300 mg per kg hydrogen peroxide comprised in the aqueous hydrogen peroxide solution, more preferably in the range from 0 to 200 mg per kg hydrogen peroxide comprised in the aqueous hydrogen peroxide solution, more preferably in the range from 0 to 100 mg per kg hydrogen peroxide comprised in the aqueous hydrogen peroxide solution.

6. The process of embodiment 4 or 5, wherein the aqueous hydrogen peroxide solution provided in (i.1) and subjected to (i.2) has a total organic carbon content (TOC) in the range from 100 to 800 mg per kg hydrogen peroxide comprised in the aqueous hydrogen peroxide solution, preferably in the range from 120 to 750 mg per kg hydrogen peroxide comprised in the aqueous hydrogen peroxide solution, more preferably in the range from 150 to 700 mg per kg hydrogen peroxide comprised in the aqueous hydrogen peroxide solution, determined as described in Reference Example 5.

7. The process of any one of embodiments 4 to 6, wherein the aqueous hydrogen peroxide solution provided in (i.1) and subjected to (i.2) has a pH in the range from 0 to 3.0, preferably in the range from 0.1 to 2.5, more preferably in the range from 0.5 to 2.3, determined as described in Reference Example 4.

8. The process of any one of embodiments 4 to 7, wherein the aqueous hydrogen peroxide solution provided in (i.1) and subjected to (i.2) comprises from 20 to 80 weight-%, preferably from 30 to 70 weight-%, more preferably from 40 to 60 weight-% of hydrogen peroxide relative to the total weight of the aqueous hydrogen peroxide solution.

9. The process of any one of embodiments 4 to 8, wherein the aqueous hydrogen peroxide solution provided in (i.1) and subjected to (i.2) is obtained or obtainable from an anthraquinone process.

10. The process of any one of embodiments 1 to 9, wherein the contacting of the reaction mixture provided in (i) in the epoxidation zone with the epoxidation catalyst according to (ii) is carried out at an absolute pressure in the epoxidation zone in the range from 0.5 to 5.0 MPa, preferably in the range from 1.5 to 3.0 MPa, more preferably in the range from 1.8 to 2.8 MPa.

11. The process of any one of embodiments 1 to 10, wherein the contacting of the reaction mixture provided in (i) in the epoxidation zone with the epoxidation catalyst according to (ii) is carried out at a temperature in the epoxidation zone in the range from 33 to 73° C., preferably in the range from 38 to 63° C., more preferably in the range from 53 to 63° C.

12. The process of any one of embodiments 1 to 11, wherein a cooling medium is used for adjusting the temperature in the epoxidation zone, wherein the temperature of the cooling medium is preferably in the range from 25 to 65° C., preferably in the range from 30 to 55° C., more preferably in the range from 345 to 55° C.

13. The process of any one of embodiments 1 to 12, wherein the weight ratio of propylene:hydrogen peroxide (w/w) in the reaction mixture provided in (i) is in the range from 1:1 to 6:1, preferably in the range from 1:1 to 2:1 or in the range from 3:1 to 5:1.

14. The process of any one of embodiments 1 to 13, wherein the weight ratio of organic solvent:hydrogen peroxide (w/w) in the reaction mixture provided in (i) is in the range from 15:1 to 5:1, preferably in the range from 12:1 to 6:1, more preferably in the range from 11:1 to 8:1.

15. The process of any one of embodiments 1 to 14, wherein the weight ratio of organic solvent:propylene (w/w) in the reaction mixture provided in (i) is in the range from 10:1 to 1:0.1, preferably in the range from 9:1 to 1:1, more preferably in the range from 9:1 to 7:1 or in the range from 1.5:1 to 1:1.

16. The process of any one of embodiments 1 to 15, wherein the epoxidation reaction conditions according to (ii) comprise trickle-bed conditions.

17. The process of any one of embodiments 1 to 16, wherein the epoxidation reaction conditions according to (ii) comprise fixed-bed conditions.

18. The process of any one of embodiments 1 to 17, wherein from 95 to 100 weight-%, preferably from 98 to 100 weight-%, more preferably from 99 to 100 weight-%, more preferably from 99.5 to 100 weight-%, more preferably from 99.9 to 100 weight-% of the zeolitic material consist of Si, O, Ti and optionally H.

19. The process of any one of embodiments 1 to 18, wherein the zeolitic material comprises Ti in an amount in the range from 0.2 to 5 weight-%, preferably in the range from 0.5 to 4 weight-%, more preferably in the range from 1.0 to 3 weight-%, more preferably in the range from 1.2 to 2.5 weight-%, more preferably in the range from 1.4 to 2.2 weight-%, calculated as elemental Ti and based on the total weight of the zeolitic material.

20. The process of any one of embodiments 1 to 19, wherein the zeolitic material is a titanium silicalite-1 (TS-1).

21. The process of any one of embodiments 1 to 20, wherein the epoxidation catalyst further comprises a binder.

22. The process of embodiment 21, wherein the epoxidation catalyst is in the form of a molding, preferably in the form of an extrudate or a granule.

23. The process of embodiment 21 or 22, wherein from 95 to 100 weight-%, preferably from 98 to 100 weight-%, more preferably from 99 to 100 weight-%, more preferably from 99.5 to 100 weight-%, more preferably from 99.9 to 100 weight-% of the molding consist of the zeolitic material and the binder.

24. The process of any one of embodiments 21 to 23, wherein from 95 to 100 weight-%, preferably from 98 to 100 weight-%, more preferably from 99 to 100 weight-%, more preferably from 99.5 to 100 weight-%, more preferably from 99.9 to 100 weight-% of the binder comprised in the molding consist of Si and O.

25. The process of embodiment 24, wherein the epoxidation catalyst, preferably the molding, comprises the binder, calculated as $SiO_2$, in an amount in the range from 2 to 90 weight-%, preferably in the range from 5 to 70 weight-%, more preferably in the range from 10 to 50 weight-%, more preferably in the range from 15 to 30 weight-%, more preferably in the range from 20 to 25 weight-%, based on the total weight of the epoxidation catalyst, preferably based on the total weight of the molding and/or wherein the epoxidation catalyst, preferably the molding, comprises the zeolitic material in an amount in the range of from 10 to 98 weight-%, preferably in the range of from 30 to 95 weight-%, more preferred in the in the range of from 50 to 90 weight-%, more preferred in the range of from 70 to 85 weight-%, more preferred in the range of from 75 to 80 weight-%, based on the total weight of the epoxidation catalyst, preferably based on the total weight of the molding.

26. The process of any one of embodiments 1 to 25, wherein at least (ii) is carried out continuously, wherein preferably at least (ii) and (iii), more preferably (i), (ii) and (iii) are carried out continuously.

27. The process of any one of embodiments 1 to 26, further comprising
(iv) separating propylene oxide from the effluent stream obtained in (iii), optionally after having separated propylene, obtaining a stream S1 comprising propylene oxide and a stream S2 comprising water and organic solvent.

28. The process of embodiment 27, wherein (iv) comprises
(iv-1) separating propylene from the effluent stream obtained in (iii) and preferably recycling at least a portion of the separated propylene, optionally after work-up, to the epoxidation zone according to (ii), obtaining a stream S1a comprising propylene oxide, water, and organic solvent and being depleted of propylene compared to the effluent stream;
(iv-2) separating propylene oxide from the stream S1a obtained according to (iv-1), obtaining a stream S1 b comprising propylene oxide and being depleted of water and the organic solvent compared to the effluent stream and stream S1a respectively, and a stream S2 comprising water and organic solvent and being depleted of propylene oxide compared to the effluent stream and S1a respectively.

29. The process of embodiment 27 or 28, comprising:
(v) separating organic solvent from stream S2 obtained according to (iv) or (iv-2) by distillation, obtaining a stream S3 enriched in organic solvent compared to stream S2 and preferably recycling at least a portion of S3, optionally after work-up, to the epoxidation zone according to (ii).

30. The process of any one of embodiments 1 to 29, wherein the organic solvent is an organic epoxidation solvent, preferably selected from the group consisting of alcohol, acetonitrile, tert-butanol, propionitrile and mixtures of two or more thereof; more preferably selected from the group consisting of alcohol, acetonitrile and mixtures of alcohol and acetonitrile, more preferred the organic solvent comprises at least an alcohol.

31. A reaction mixture for preparing propylene oxide, comprising propylene, water, organic solvent, and hydrogen peroxide, wherein the reaction mixture comprises at least one aliphatic oxygen containing compound having 8 to 10 carbon atoms in an amount of at most 500 mg per kg hydrogen peroxide comprised in the reaction mixture.

32. The reaction mixture of embodiment 31, comprising the at least one aliphatic oxygen containing compound having 8 to 10 carbon atoms in an amount in the range from 0 to 500 mg per kg hydrogen peroxide comprised in the reaction mixture, preferably in the range from 0 to 440 mg per kg hydrogen peroxide comprised in the reaction mixture, more preferably in the range from 0 to 300 mg per kg hydrogen peroxide comprised in the reaction mixture, more preferably in the range from 0 to 200 mg per kg hydrogen peroxide comprised in the reaction mixture, more preferably in the range from 0 to 100 mg per kg hydrogen peroxide comprised in the reaction mixture.

33. The reaction mixture of embodiment 31 or 32, being obtainable or obtained by a process comprising, preferably consisting of (i) as defined in any one of embodiments 1 to 9.

34. A process for preparing a reaction mixture according to any one of embodiments 31 to 33, wherein the reaction mixture comprises, preferably consists of (i) as defined in any one of embodiments 1 to 9.

35. A catalytic epoxidation system for preparing propylene oxide, the catalytic epoxidation system comprising an epoxidation catalyst comprising a zeolitic material having a framework structure comprising Si, O, and Ti, and further comprising the reaction mixture comprising propylene, water, and organic solvent according to any one embodiments 31 to 34.

36. The catalytic epoxidation system of embodiment 35, obtainable or obtained by a process comprising providing a reaction mixture according to any one of embodiments 31 to 34 and bringing said reaction mixture in contact with the zeolitic material having a framework structure comprising Si, O, and Ti.

37. A process for preparing the catalytic epoxidation system according to embodiment 35, comprising providing a reaction mixture according to any one of embodiments 31 to 34 and bringing said reaction mixture in contact with the zeolitic material having a framework structure comprising Si, O, and Ti.

38. Use of an aqueous hydrogen peroxide solution as epoxidation agent for preparing propylene oxide in the presence of an organic solvent and an epoxidation catalyst comprising a zeolitic material having a framework structure comprising Si, O, and Ti, wherein the aqueous hydrogen peroxide solution comprises at least one aliphatic oxygen containing compound having 8 to 10 carbon atoms in an amount of at most 500 mg per kg hydrogen peroxide comprised in the aqueous hydrogen peroxide solution.

It is explicitly noted that the preceding set of embodiments is not the set of claims determining the extent of protection, but represents a suitably structured part of the description directed to general and preferred aspects of the present invention.

The present invention is further illustrated by the following reference examples, comparative examples, and examples.

EXAMPLES

Reference Example 1—Experimental Setup

In a continuous epoxidation reaction setup, a vertically arranged tubular reactor (length: 1.4 m, outer diameter 10 mm, internal diameter: 4 mm; material: stainless austenitic steel of type 1.4571) equipped with a cooling jacket for thermostatization, was charged with 15 g of the moldings of the respective TS-1 catalyst in the form of strands as described in the respective Reference Examples below. The area within the reactor covered by the moldings is called the catalyst bed. The remaining reactor volume was filled with inert material (steatite spheres, 2 mm in diameter) to a height of about 5 cm at the lower end of the reactor and the remainder at the top end of the reactor. The temperature in the epoxidation zone (=catalyst bed) was measured with a tenfold thermocouple (ten thermoelements, each made of stainless austenitic steel of type 1.4571). Six of the ten thermoelements were located in the first half of the catalyst bed. Feed streams were provided for all starting materials methanol, propylene and hydrogen peroxide (employed as aqueous hydrogen peroxide solution with a hydrogen peroxide content of 40 weight-% or 60 weight-%). Initially, all feed streams contained less than 0.1 weight-% of aliphatic oxygen containing compounds having 8 to 10 carbon atoms. An aliphatic oxygen containing compound having 9 carbon atoms was added to the hydrogen peroxide feed stream as indicated below in the Examples in detail.

The feed streams were combined and fed to the reactor. The combination of all feed streams is referred to as "reaction mixture".

Via the cooling medium passed through the cooling jacket, which had a temperature in the range from 45 to 55° C., the temperature in the epoxidation zone was adjusted in the range from 53 to 63° C. so that the hydrogen peroxide conversion, determined on the basis of the effluent stream leaving the reactor, was essentially constant at a pre-determined value. The pressure within the reactor was held constant at 21 bar(abs).

The reactor effluent stream downstream the pressure control valve was collected, weighed and analyzed. The hydrogen peroxide content was determined colorimetrically using the titanyl sul-fate method. All other components were quantified by gas chromatography. The selectivity for propylene oxide (S(H$_2$O$_2$) to PO) given was determined relative to hydrogen peroxide (H$_2$O$_2$), and was calculated as 100 times the ratio of moles of propylene oxide in the effluent stream (mol (PO produced)) divided by the moles of hydrogen peroxide in the feed (mol (H$_2$O$_2$ feed)) as follows:

$$S(H_2O_2) \text{ to } PO = \frac{\text{mol (PO produced)}}{\text{mol (H2O2 feed)}} \times 100$$

The aliphatic oxygen containing compound having 9 carbon atoms, which was added to the hydrogen peroxide stream, consisted mainly of diisobutyl carbinol (DIBC) and had the following detailed composition: 85.8 weight-% 2,6-dimethyl-4-heptanol, 12.8 weight-% 4,6-dimethyl-2-heptanol, and 0,2 weight-% 2,6-dimethyl-4-heptanon, the remaining residue up to 100 weight-% being impurities.

The composition of the aliphatic oxygen containing compound having 9 carbon atoms was determined by GC/MS, in detail according to Analytical Sciences Standard Operating Procedure MS-SOP-004.00. A one-tenth (0.1) microliter (nominal volume) aliquot of the neat sample was analyzed on a Finnigan SSQ 7000 GC/MS system operating in the electron impact (EI) mode. A one-tenth (0.1) microliter (nominal volume) aliquot of the neat sample was analyzed in positive ion chemical ionization (PCI) mode using the same instrument. Ammonia (NH$_3$) was used as the reactant gas in the PCI analysis and was present at an ion source pressure of approximately 1300 millitorr. Representative analysis conditions are listed below:

Column: J&W Scientific 60 m×0.32 mm×1.0 μm DB-1
Temperatures: Column: 100° C. to 260° C. at 10° C./min, hold 5 min
Injector: 260° C., Ion source: 150° C.
Transfer line: 260° C., Manifold: 70° C.
Detector: EMULT: 900 V (EI), 950 V (PCI)
Preamp: 10-7 A/V
Conv. Dyn.: (±)15 kV, Mode: +Q1MS, CENT
ELEN: 70 V (EI), 200 V (PCI), ECURR: 1.3 mA (EI), 1.0 mA (PCI)
Scan: 35-650 amu (EI), Scan: 65 to 650 amu (PCI), Rate: 0.5 sec/scan Injection: Volume (nominal): 0.1 μL (EI), 0.1 μL (PCI)
Split ratio: 300/1
FT In view of the two isomers of diisobutyl carbinol forming more than 98.5 weight-% of the weight of the aliphatic oxygen containing compound having 9 carbon atoms, the latter is in the following abreviated "DIBC".

Reference Example 2—TS-1 Catalyst 1

A titanium silicalite-1 (TS-1 catalyst 1) powder was prepared according to the following recipe: TEOS (tetraethyl orthosilicate) (300 kg) were loaded into a stirred tank reactor at room temperature and stirring (100 r.p.m.) was started. In a second vessel, 60 kg TEOS and 13.5 kg TEOT (tetraethyl orthotitanate) were first mixed and then added to the TEOS in the first vessel. Subsequently, another 360 kg TEOS were added to the mixture in the first vessel. Then, the content of the first vessel was stirred for 10 min before 950 g TPAOH (tetrapropylammonium hydroxide) were added. Stirring was continued for 60 min. Ethanol released by hydrolysis was separated by distillation at a bottoms temperature of 95° C. 300 kg water were then added to the content of the first vessel, and water in an amount equivalent to the amount of distillate was further added. The obtained mixture was stirred for 1 h. Crystallization was performed at 175° C. within 12 h at autogenous pressure. The obtained titanium silicalite-1 crystals were separated, dried, and calcined at a temperature of 500° in air for 6 h. The obtained particles of the zeolitic material exhibited a Ti content of 1.9 weight-%, calculated as elemental Ti.

The particles of the zeolitic material and carboxymethyl cellulose (4.0 g; Walocel™, Mw=15,000 g) were mixed in a kneader for 5 min. Then, an aqueous polystyrene dispersion (100.7 g; 33.7 g polystyrene) was continuously added. After 10 min, polyethylene oxide (1.33 g) was added. After 10 min, an aqueous colloidal silica binder precursor (70 g; 40 weight-% SiO$_2$; Ludox® AS-40) was added. After a further 10 min, 20 ml water were added. The total kneading time was 35 min. The resulting formable mass obtained from kneading, having a plasticity of 3321 N, was extruded at a pressure of 100 bar through a matrix having circular holes with a diameter of 1.9 mm. The obtained strands were dried in air in an oven at a temperature of 120° C. for 4 h and calcined in air at a temperature of 490° C. for 5 h. The crushing strength of the strands determined as described hereinabove was 1.6 N.

36 g of these strands were mixed in four portions of each 9 g with 180 g deionized water per portion. The resulting mixtures were heated to a temperature of 145° C. for 8 h in an autoclave. Thereafter, the obtained water-treated strands were separated and sieved over a 0.8 mm sieve. The obtained strands were then washed with deionized water and subjected to a stream of nitrogen at ambient temperature. The respectively washed strands were subsequently dried in air at a temperature of 120° C. for 4 h and then calcined in air at a temperature of 450° C. for 2 h. The resulting material had a TOC of less than 0.1 g/100 g, a Si content of 44 g/100 g, and a Ti content of 1.5 g/100 g.

Reference Example 3—TS-1 Catalyst 2

TS-1 catalyst 2 was synthesized according to Example 5 of EP 1 138 387 A1. 2 mm extrudates were prepared using silica sol as binder.

Reference Example 4—pH Measurement pH measurements were done with a pH sensitive glass electrode according to AM7160. The pH is to be understood as being determined using a pH sensitive glass electrode wherein the liquid aqueous system is in an inert atmosphere which avoids, for example, that the liquid aqueous system comes into contact with atmospheric carbon dioxide which, if absorbed in the liquid aqueous system, would reduce the pH.

Reference Example 5—Determination of Total Organic Carbon (TOC)

The total organic carbon content (TOC) was determined according to DIN EN 1484.

Reference Example 6—Determination of $N_2$ Adsorption/Desorption Isotherms

The nitrogen adsorption/desorption isotherms were determined at 77 K according to the method disclosed in DIN TS-1 catalyst 1 from Reference Example 2 was used as epoxidation catalyst.

Via the cooling medium passed through the cooling jacket, the average temperature in the epoxidation zone was adjusted in the range from 60 to 70° C. so that the hydrogen peroxide conversion, determined on the basis of the effluent stream leaving the reactor, was essentially constant at ≥90%. The pressure within the reactor was held constant at 21 bar(abs), and the reaction mixture—apart from the fixed-bed catalyst—consisted of one single liquid phase. Epoxidation was conducted for 550 h.

The resulting selectivity towards propylene oxide (PO) ($S(H_2O_2)$ to PO, calculated according to Reference Example 1) based on the data measured at the end of the epoxidation (at 550 h), the temperature of the cooling medium and the average temperature in the epoxidation zone are indicated in Table 1.

TABLE 1

| | Epoxidation of propylene to propylene oxide in the presence of different DIBC concentrations | | | | |
|---|---|---|---|---|---|
| | DIBC concentration | | | | $T_{average}$ |
| No. | [weight-% based on weight of $H_2O_2$] | [mg DIBC per kg $H_2O_2$] | $S(H_2O_2)$ to PO [%] | T cooling medium [° C.] | epoxidation zone [° C.] |
| i | 0.01 | 100 | 90 | 53 | 63 |
| ii | 0.05 | 500 | 90 | 53 | 62 |
| iii* | 0.10 | 1,000 | 83 | 58 | 66 |
| iv* | 0.50 | 5,000 | 81 | 59 | 67 |
| v* | 1.00 | 10,000 | 80 | 60 | 67 |

*comparative example

66131. The isotherms, at the temperature of liquid nitrogen, were measured using Micrometrics ASAP 2020M and Tristar system.

Example 1—Epoxidation of Propylene Using Different Diisobutyl Carbinol (DIBC) Concentrations Epoxidation of propylene was carried out according to Reference Example 1. An aqueous $H_2O_2$ solution with 40 weight-% was used as hydrogen peroxide feed stream, which contained less than 0.1 weight-% of aliphatic oxygen containing compounds having 8 to 10 carbon atoms based on $H_2O_2$, and had a TOC value of 700 mg per kg hydrogen peroxide, determined according to Reference Example 5, as well as a pH value of 2, measured according to Reference Example 4.

DIBC was added to the aqueous $H_2O_2$ solution so that the DIBC concentration relative to the weight of hydrogen peroxide in the aqueous $H_2O_2$ solution feed stream and also in the reaction mixture at the beginning of the epoxidation reaction was as indicated in Table 1.

Through the reactor, the starting materials were passed with the following flow rates: methanol (77.8 g/h); hydrogen peroxide (7.6 g/h; employed as aqueous hydrogen peroxide solution with a hydrogen peroxide content of 40 weight-%, i.e. flow rate of the aqueous hydrogen peroxide solution: 19.4 g/h); propylene (10.8 g/h; polymer grade). The overall flow rate of the combined feed streams was 108 g/h.

The experiments i to v showed that the catalyst performance increased with decreasing DIBC concentration. Increase in selectivity was most pronounced when DIBC concentration was de-creased from 0.1 to 0.05 weight-% based on $H_2O_2$. The reaction gave the best result a DIBC concentration ≤0.1 weight-%. At DIBC concentrations above 500 mg DIBC per kg hydrogen peroxide, a much higher temperature in the epoxidation zone (and thus a higher temperature of the cooling medium) was required in order to keep the hydrogen peroxide conversion at a value of ≥90%. However, at these high DIBC concentrations, selectivity was well below 85%.

Example 2—Epoxidation of Propylene Using TS-1 Catalyst 2

The experiment was carried out according to experiment no. v from Example 1 but with TS-1 catalyst 2 from Reference Example 3, with a 40 weight-% $H_2O_2$ aqueous solution. The DIBC concentration in the hydrogen peroxide feed stream and also in the reaction mixture at the beginning of the epoxidation reaction, the resulting selectivity towards propylene oxide (PO) in the effluent stream ($S(H_2O_2)$ to PO, calculated according to Reference Example 1), the temperature of the cooling medium and the average temperature in the epoxidation zone are indicated in Table 2.

TABLE 2

| | DIBC concentration [weight-% based on weight of $H_2O_2$] | | | | $T_{average}$ | |
| No. | [weight-% based on weight of $H_2O_2$] | [mg DIBC per kg $H_2O_2$] | $S(H_2O_2)$ to PO [%] | T cooling medium [° C.] | Epoxidation zone [° C.] |
| --- | --- | --- | --- | --- | --- |
| vii | 0.05 | 500 | 92 | 52 | 59 |
| viii* | 0.1 | 1,000 | 91 | 58 | 64 |

*comparative example

Results of experiment viii were comparable to the results from experiment t no. v from Example 1: A too high concentration of DIBC of more than 500 mg per kg hydrogen peroxide —here 1000 mg per kg hydrogen peroxide— negatively affected different types of TS-1 zeolite catalysts, independent from their mode of preparation and characteristics.

Example 3—Epoxidation of Propylene without Temperature Adjustment

Epoxidation of propylene was carried out according to Example 1 with an aqueous $H_2O_2$ solution with 40 weight-% and TS-1 catalyst 1 as epoxidation catalyst; the aliphatic oxygen containing compound having 9 carbon atoms was added to the hydrogen peroxide feed stream as in Example 1 at a concentration as indicated in Table 4.

Via the cooling medium passed through the cooling jacket, the temperature in the epoxidation zone was adjusted at the beginning of the epoxidation reaction in the range from 53 to 63° C. so that the hydrogen peroxide conversion, determined on the basis of the effluent stream leaving the reactor, was essentially constant at ≥98%, i.e. the temperature of the cooling medium was set in the range from 45 to 55° C. After the beginning of the epoxidation reaction, no further ad-justments of the temperature in the epoxidation zone via the cooling medium were made. Epoxidation was conducted until the temperature in the epoxidation zone exceeded 63° C. (and respectively, the temperature of the cooling medium exceeded 55° C.), then the reaction was stopped. The time from the beginning of the epoxidation reaction until the stop was measured.

The resulting selectivity towards propylene oxide (PO) in the effluent stream ($S(H_2O_2)$ to PO, calculated according to Reference Example 1, determined on the data measured at the time when the epoxidation was stopped and the time until the reaction was stopped are indicated in Table 3.

TABLE 3

| | Epoxidation of propylene with temperature of the cooling medium in the range from 45 to 55° C. | | |
| No. | DIBC [weight-% based on weight of $H_2O_2$] | $S(H_2O_2)$ to PO [%] | $t_{until\ reaction\ stop}$ [h] |
| --- | --- | --- | --- |
| ix | 0.05 | 97 | 220 |
| x* | 0.10 | 96 | 92 |

*comparative example

Experiments x and xi showed that a high hydrogen peroxide conversion of ≥98% and a high selectivity (optimal temperature window) could only be achieved over a meaningful period of time, i.e. for more than 200 hours, if the concentration of the DIBC was kept at or below the threshold of 500 ppm.

Cited Literature

Ullmann's Encyclopedia of Industrial Chemistry, 5′h edition, volume A 13 (1989) pages 443-466
EP 1 546 035 A1
WO 99/40024 A1
WO 2013/160163 A1
EP1122249 A1
WO 2015/049327 A1
Stallmach et al. in Annual Reports on NMR Spectroscopy 2007, Vol. 61, pp. 51-131

The invention claimed is:

1. A process for the preparation of propylene oxide, comprising
    (i) providing a reaction mixture comprising propylene, water, organic solvent, and hydrogen peroxide;
    (ii) contacting the reaction mixture provided in (i) in an epoxidation zone with an epoxidation catalyst comprising a zeolitic material having a framework structure comprising Si, O, and Ti, and subjecting the reaction mixture to epoxidation reaction conditions in the epoxidation zone, obtaining, in the epoxidation zone, a mixture comprising propylene oxide, water, and organic solvent;
    (iii) removing an effluent stream from the epoxidation zone, the effluent stream comprising propylene oxide, water, and organic solvent;
    wherein the reaction mixture provided in (i) and subjected to (ii) comprises in an amount of at most 500 mg per kg hydrogen peroxide comprised in said reaction mixture at least one aliphatic oxygen containing compound having 8 to 10 carbon atoms;
    wherein the at least one aliphatic oxygen containing compound having 8 to 10 carbon atoms is selected from the group consisting of secondary mono alcohols $C_9H_{20}O$, mono ketones $C_9H_{18}O$, and mixtures of secondary mono alcohols $C_9H_{20}O$ and mono ketones $C_9H_{18}O$;
    and comprises at least diisobutyl carbinol.

2. The process of claim 1, wherein the reaction mixture provided in (i) and subjected to (ii) contains the at least one aliphatic oxygen containing compound having 8 to 10 carbon atoms in an amount in the range from 0 to 500 mg per kg hydrogen peroxide comprised in the reaction mixture.

3. The process of claim 1, wherein providing the reaction mixture in (i) comprises
    (i.1) providing an aqueous hydrogen peroxide solution;
    (i.2) admixing the aqueous hydrogen peroxide solution provided in (i.1) with propylene and organic solvent, obtaining the reaction mixture;
    wherein the aqueous hydrogen peroxide solution provided in (i.1) and subjected to (i.2) contains the at least one aliphatic oxygen containing compound having 8 to 10 carbon atoms in an amount of at most 500 mg per kg hydrogen peroxide comprised in the reaction mixture.

4. The process of claim 3, wherein the aqueous hydrogen peroxide solution provided in (i.1) and subjected to (i.2) contains the at least one aliphatic oxygen containing compound having 8 to 10 carbon atoms in an amount in the range from 0 to 500 mg per kg hydrogen peroxide comprised in the aqueous hydrogen peroxide solution.

5. The process of claim 3, wherein the aqueous hydrogen peroxide solution provided in (i.1) and subjected to (i.2) has a total organic carbon content (TOC) in the range from 100 to 800 mg per kg hydrogen peroxide comprised in the aqueous hydrogen peroxide solution, determined according to DIN EN 1484.

6. The process of claim 3, wherein the aqueous hydrogen peroxide solution provided in (i.1) and subjected to (i.2) is obtained from an anthraquinone process.

7. The process of claim 1, wherein the epoxidation reaction conditions according to (ii) comprise trickle-bed conditions or wherein the epoxidation reaction conditions according to (ii) comprise fixed-bed conditions.

8. The process of claim 1, wherein (ii) is carried out continuously.

9. A reaction mixture for preparing propylene oxide, comprising propylene, water, organic solvent, and hydrogen peroxide, wherein the reaction mixture comprises at least one aliphatic oxygen containing compound having 8 to 10 carbon atoms in an amount of at most 500 mg per kg hydrogen peroxide comprised in the reaction mixture;

wherein the at least one aliphatic oxygen containing compound having 8 to 10 carbon atoms is selected from the group consisting of secondary mono alcohols $C_9H_{20}O$, mono ketones $C_9H_{18}O$, and mixtures of secondary mono alcohols $C_9H_{20}O$ and mono ketones $C_9H_{18}O$;

and comprises at least one diisobutyl carbinol.

10. The reaction mixture of claim 9, being obtained by a process comprising providing a reaction mixture comprising propylene, water, organic solvent, and hydrogen peroxide.

11. A catalytic epoxidation system for preparing propylene oxide, the catalytic epoxidation system comprising an epoxidation catalyst comprising a zeolitic material having a framework structure comprising Si, O, and Ti, and further comprising the reaction mixture comprising propylene, water, and organic solvent according to claim 9.

12. The process of claim 1, wherein the material having a framework structure comprising Si, O, and Ti comprised in the epoxidation catalyst is a titanium zeolite having an MFI framework type, or an MWW framework type.

13. The process of claim 1, wherein the material having a framework structure comprising Si, O, and Ti is a titanium silicalite-1 (TS-1)).

14. The process of claim 1, wherein the organic solvent comprises at least an alcohol.

15. The process of claim 1, wherein the organic solvent comprises at least an alcohol which comprises C1 to C5 mono alcohol or a mixture of two or more C1 to C5 alcohols.

16. The process of claim 1, wherein the organic solvent is an alcohol which comprises methanol.

* * * * *